(12) United States Patent
Lee et al.

(10) Patent No.: US 6,235,023 B1
(45) Date of Patent: *May 22, 2001

(54) CELL NECROSIS APPARATUS

(75) Inventors: Kee S. Lee, Daly City; Daniel Balbierz, Redwood City, both of CA (US)

(73) Assignee: Rita Medical Systems, Inc., Mountain View, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/148,571

(22) Filed: Sep. 4, 1998

Related U.S. Application Data

(63) Continuation-in-part of application No. 09/047,845, filed on Mar. 25, 1998, now Pat. No. 5,980,517, which is a continuation-in-part of application No. 09/020,182, filed on Feb. 6, 1998, now abandoned, which is a continuation-in-part of application No. 08/963,239, filed on Nov. 3, 1997, which is a continuation-in-part of application No. 08/515,379, filed on Aug. 15, 1995, now Pat. No. 5,683,384.

(51) Int. Cl.[7] ..................................................... A61B 18/18
(52) U.S. Cl. ............................................. 606/41; 607/101
(58) Field of Search ................................. 606/41, 42, 45, 606/48–50; 607/101, 102; 604/21, 22

(56) References Cited

U.S. PATENT DOCUMENTS

| 5,370,675 | * | 12/1994 | Edwards et al. | ...................... 607/101 |
| 5,685,839 | | 11/1997 | Edwards et al. . | |
| 5,817,092 | * | 10/1998 | Behl | ....................................... 606/41 |
| 5,855,576 | * | 1/1999 | LeVeen et al. | .......................... 606/41 |

FOREIGN PATENT DOCUMENTS

| WO 96/29946 | 10/1996 | (WO) . |
| WO 97/06855 | 2/1997 | (WO) . |

* cited by examiner

*Primary Examiner*—Michael Peffley
(74) *Attorney, Agent, or Firm*—Wilson Sonsini Goodrich & Rosati

(57) ABSTRACT

A cell necrosis apparatus includes an introducer with a distal end sufficiently sharp to penetrate tissue. An energy delivery device has a first set of RF electrodes, a second set of RF electrodes and a third RF electrode. Each of electrodes has a tissue piercing distal end and is positionable in the introducer as the introducer is advanced through tissue. The first and second sets of RF electrodes are deployable with curvature from the introducer. The third RF electrode is deployable from the introducer with less curvature than the first and second sets of RF electrodes. The second set of RF electrodes is deployable a greater distance from the introducer than the first set of RF electrodes.

56 Claims, 16 Drawing Sheets

CELL NECROSIS APPARATUS

REFERENCE TO RELATED APPLICATIONS

This application is a continuation-in-part application of Ser. No. 09/047,845, filed Mar. 25, 1998, now U.S. Pat. No. 5,980,517, which is a continuation-in-part of Ser. No. 09/020,182, filed Feb. 6, 1998, (now abandoned) which is a continuation-in-part of Ser. No. 08/963,239, filed Nov. 3, 1997, which is a continuation-in-part of Ser. No. 08/515,379, filed Aug. 15, 1995, now U.S. Pat. No. 5,683,384, all incorporated herein by reference.

BACKGROUND OF THE INVENTION

1. Field of the Invention

This invention relates generally to a cell necrosis apparatus, and more particularly to a cell necrosis apparatus with an introducer and deployable electrodes.

2. Description of the Related Art

Current open procedures for treatment of tumors are extremely disruptive and cause a great deal of damage to healthy tissue. During the surgical procedure, the physician must exercise care in not cutting the tumor in a manor that creates seeding of the tumor, resulting in metastasis. In recent years, development of products has been directed with an emphasis on minimizing the traumatic nature of traditional surgical procedures.

There has been a relatively significant amount of activity in the area of hyperthermia as a tool for treatment of tumors. It is known that elevating the temperature of tumors is helpful in the treatment and management of cancerous tissues. The mechanisms of selective cancer cell eradication by hyperthermia are not completely understood. However, four cellular effects of hyperthermia on cancerous tissue have been proposed, (i) changes in cell or nuclear membrane permeability or fluidity, (ii) cytoplasmic lysomal disintegration, causing release of digestive enzymes, (iii) protein thermal damage affecting cell respiration and the synthesis of DNA or RNA and (iv) potential excitation of immunologic systems. Treatment methods for applying heat to tumors include the use of direct contact radio-frequency (RF) applicators, microwave radiation, inductively coupled RF fields, ultrasound, and a variety of simple thermal conduction techniques.

Among the problems associated with all of these procedures is the requirement that highly localized heat be produced at depths of several centimeters beneath the surface of the skin.

Attempts to use interstitial local hyperthermia have not proven to be very successful. Results have often produced nonuniform temperatures throughout the tumor. It is believed that tumor mass reduction by hyperthermia is related to thermal dose. Thermal dose is the minimum effective temperature applied throughout the tumor mass for a defined period of time. Because blood flow is the major mechanism of heat loss for tumors being heated, and blood flow varies throughout the tumor, more even heating of tumor tissue is needed to ensure effective treatment.

The same is true for ablation of the tumor itself through the use of RF energy. Different methods have been utilized for the RF ablation of masses such as tumors. Instead of heating the tumor it is ablated through the application of energy. This process has been difficult to achieve due to a variety of factors including, (i) positioning of the RF ablation electrodes to effectively ablate all of the mass, (ii) introduction of the RF ablation electrodes to the tumor site and (iii) controlled delivery and monitoring of RF energy to achieve successful ablation without damage to non-tumor tissue.

Thus, non-invasive procedures for providing heat to internal tissue have had difficulties in achieving substantial specific and selective treatment.

Examples illustrating the use of electromagnetic energy to ablate tissue are disclosed in: U.S. Pat. No. 4,562,200; U.S. Pat. No. 4,411,266; U.S. Pat. No. 4,838,265; U.S. Pat. No. 5,403,311; U.S. Pat. No. 4,011,872; U.S. Pat. No. 5,385,544; and U.S. Pat. No. 5,385,544.

There is a need for a cell necrosis apparatus with at least two electrodes that are deployable with curvature from an introducer. There is another need for a cell necrosis apparatus with at least two electrodes that are selectably deployable with curvature from an introducer to a desired deployed geometric configuration. There is yet a further need for a cell necrosis apparatus that provides deployable electrodes that create a variety of different geometric cell necrosis lesions.

SUMMARY OF THE INVENTION

Accordingly, an object of the invention is to provide a cell necrosis apparatus that provides tissue reduction at selected anatomical sites.

Another object of the invention is to provide a treatment apparatus to create cell necrosis.

Still another object of the invention is to provide a cell necrosis apparatus that has at least two electrodes which are deployable from an introducer with curvature and a third electrode which is deployable with minimal curvature.

Yet another object of the invention is to provide a cell necrosis apparatus with selectively deployed electrodes.

A further object of the invention is to provide a cell necrosis apparatus that is configured to deploy electrodes selectively at a tissue site to create a desired cell necrosis lesion.

These and other objects of the invention are achieved in a cell necrosis apparatus including an introducer with a distal end sufficiently sharp to penetrate tissue. An energy delivery device has a first set of RF electrodes, a second set of RF electrodes and a third RF electrode. Each of electrodes has a tissue piercing distal end and is positionable in the introducer as the introducer is advanced through tissue. The first and second sets of RF electrodes are deployable with curvature from the introducer. The third RF electrode is deployable from the introducer with less curvature than the first and second sets of RF electrodes. The second set of RF electrodes is deployable a greater distance from the introducer than the first set of RF electrodes.

In another embodiment, a cell necrosis apparatus has an energy delivery device that includes a first RF electrode with a tissue piercing distal portion and a second RF electrode with a tissue piercing distal portion. The first and second RF electrodes are positionable in the introducer as the introducer is advanced through tissue and deployable with curvature from the introducer at a selected tissue site. A groundpad electrode is coupled to the first and second RF electrodes. A first sensor is coupled to the groundpad electrode.

BRIEF DESCRIPTION OF THE FIGS.

DETAILED DESCRIPTION

Figure 1:
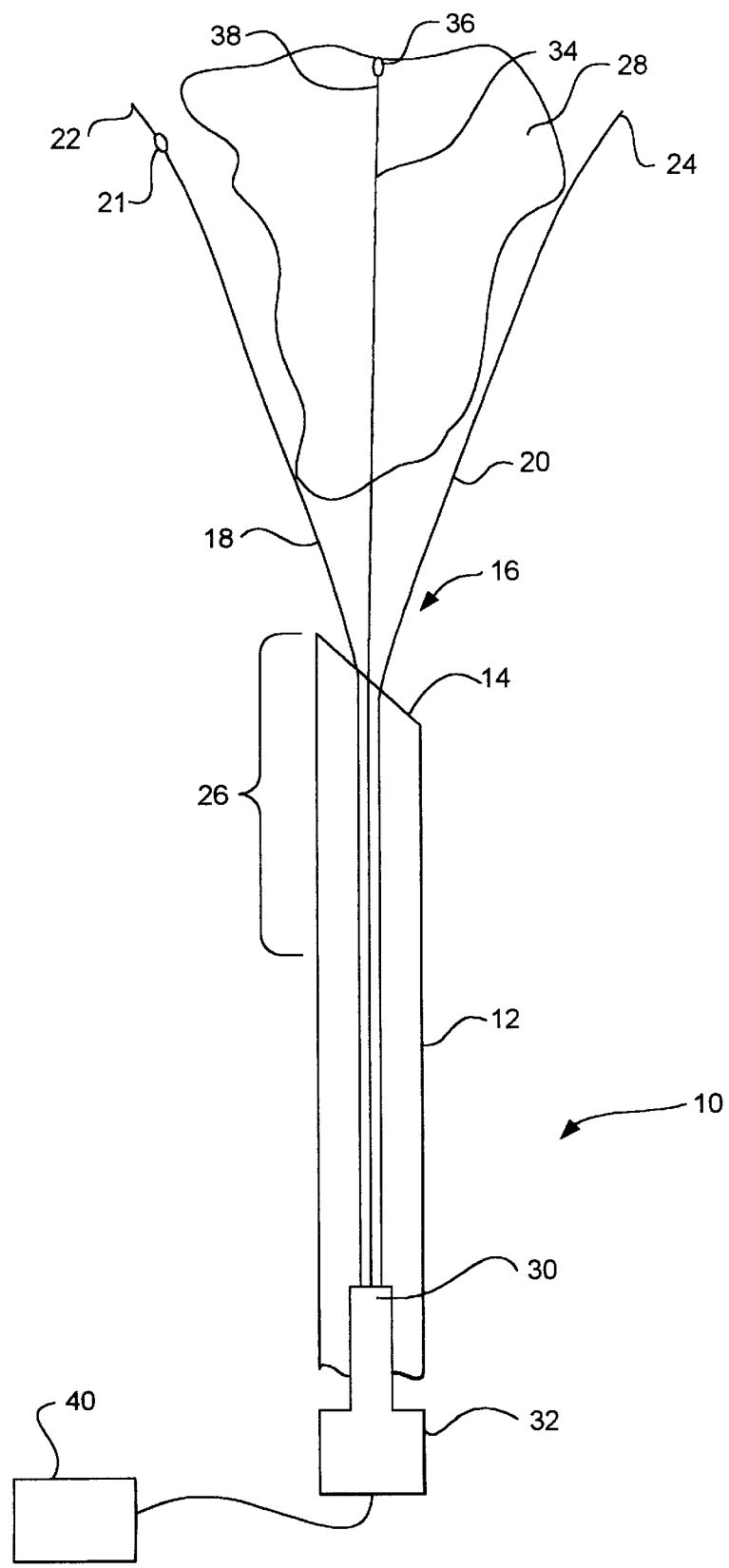
FIG. 1 is cross-sectional view of a cell necrosis apparatus of the present invention with two deployable electrodes and an deployable member at a selected cell necrosis tissue site.

Referring to FIG. 1, one embodiment of a cell necrosis apparatus 10 includes an introducer 12 with a distal end 14 sufficiently sharp to penetrate tissue. An energy delivery device, generally denoted as 16, includes a first RF electrode 18 and a second RF electrode 20. Electrodes 18 and 20 are positionable in introducer 12 as introducer 12 advances through tissue. Electrodes 18 and 20 have tissue piercing distal ends 22 and 24, respectively. Electrodes 18 and 20 are selectably deployed with curvature from a distal end 14 or a side port formed in a distal portion 26 of introducer 12 to a selected tissue site 28. Tissue site 28 can be any tissue mass and can be a tumor to be ablated. Electrodes 18 and 20 are selectably deployed to be controllably positioned at a desired location relative to tissue site 28 that includes internal placement, external placement at a periphery of tissue site 28 and at any desired location relative to tissue site 28. The selectable deployment of electrodes 18 and 20 can be achieved with the amount of advancement of electrodes 18 and 20 from introducer 12, independent advancement of electrodes 18 and 20 from introducer 12, the lengths and/or sizes of energy delivery surfaces of electrodes 18 and 20, the variation in materials used for electrodes 18 and 20 as well as variation of geometric configuration of electrodes 18 and 20 in their deployed states.

Electrodes 18 and 20 are in compacted positions while they are positioned in introducer 12. As electrodes 18 and 20 are advanced from introducer 12 they move to a deployed state from their compacted configurations. Any number of electrodes can be included in energy delivery device 16. The electrodes of energy delivery device 16 can be deployed simultaneously, in pairs, in sets and one at a time. An electrode advancement member 30 is coupled to energy delivery device 16. Electrode advancement member 30 can be actuated by the physician by movement of a proximal end 32 relative to a longitudinal axis of introducer 12.

Introducer 12 can be flexible. In one embodiment, introducer 12 is sufficiently flexible to pierce tissue, and move in any desired direction through tissue to tissue site 28. In another embodiment, introducer 12 is sufficiently flexible to reverse its direction of travel and move in direction back upon itself. In one embodiment, introducer 12 is more flexible than electrodes 18 and 20.

When introducer 12 reaches tissue site 28, including but not limited to a solid lesion, energy delivery device 16 is deployed preferably from distal end 14 of introducer 12. Energy delivery device 16 can also be deployed from side ports formed in the body of introducer 12. In the deployed state energy delivery device 16 becomes expanded from its compacted configuration in introducer 12 and is selectively positioned relative to tissue site 12. Electrodes 18 and 20 can be portioned within an interior of tissue site 12, at the exterior of tissue site 12 as well as combinations thereof. Electrodes 18, 20 as well as third, fourth, fifth, etc. electrodes are advanceable different lengths from distal end 14 of introducer 12. In one embodiment, the electrodes of deployed energy delivery device 16 are positioned equally distant a central axis of tissue site 28. Volumetric cell necrosis can proceed from the interior, exterior of tissue site 28 as well as various combinations thereof with each deployed electrode of energy delivery device 16 in order to create a selectable and predictable cell necrosis.

Electrodes 18 and 20 can be made of a variety of conductive materials, both metallic and non-metallic. One suitable material is type 304 stainless steel of hypodermic quality. In some applications, all or a portion of electrodes 18 and 20 can be made of a shaped memory metal, such as NiTi, commercially available from Raychem Corporation, Menlo Park, Calif. A radiopaque marker 21 can be coated on electrodes 18 and 20 for visualization purposes.

Electrodes 18 and 20 can have different lengths that are advanced from distal end 14 of introducer 12. The lengths can be determined by the actual physical length of electrodes 18 and 20, the length of an energy delivery surface of electrodes 18 and 20 and the length of electrodes 18 and 20 that is not covered by an insulator. Suitable lengths include but are not limited to 17.5 cm, 25.0 cm. and 30.0 cm. The actual lengths of electrodes 18 and 20 depends on the location of tissue site 28 to be ablated, its distance from the skin, its accessibility as well as whether or not the physician chooses a laparoscopic, percutaneous or other procedure.

A deployable member 34 can be coupled to electrode advancement member 30. Deployable member 34 can provide a variety of different functions including but not limited to the placement of a sensor at a selected tissue site to measure/monitor temperature and/or impedance. Additionally, all or a portion of deployable member 34 can be an RF electrode operable in bi-polar or mono-polar modes. Deployable member 34 can also be a groundpad electrode.

A sensor 36 can be coupled to deployable member 34 at a distal end 38, or at any physical location of deployable member 34. In this manner, temperature and/or impedance is measured or monitored at a distal portion of tissue site 28 or at any position in or external to tissue site 28. Deployable member 34 is deployable from distal end 14 of introducer 12 with less curvature than electrodes 18 and 20. Deployable member 34 can be deployable from distal end 14 without substantially any curvature.

Sensor 36 permits accurate measurement of temperature at tissue site 28 in order to determine, (i) the extent of cell necrosis, (ii) the amount of cell necrosis, (iii) whether or not further cell necrosis is needed and (iv) the boundary or periphery of the ablated mass. Further, sensor 36 reduces non-targeted tissue from being destroyed or ablated.

Sensor 36 is of conventional design, including but not limited to thermistors, thermocouples, resistive wires, and the like. A suitable thermal sensor 36 includes a T type thermocouple with copper constantene, J type, E type, K type, fiber optics, resistive wires, thermocouple IR detectors, and the like. It will be appreciated that sensor 36 need not be a thermal sensor.

Sensor 36 measures temperature and/or impedance to permit monitoring and a desired level of cell necrosis to be achieved without destroying too much tissue. This reduces damage to tissue surrounding the targeted mass to be ablated. By monitoring the temperature at various points within and outside of the interior of tissue site 28, a determination of the selected tissue mass periphery can be made, as well as a determination of when cell necrosis is complete. If at any time sensor 36 determines that a desired cell necrosis temperature is exceeded, then an appropriate feedback signal is received at an energy source 40 coupled to energy delivery device 16 which then regulates the amount of electromagnetic energy delivered to electrodes 18 and 20.

Energy source 40 can be an RF power supply, an ultrasound energy source, a microwave generator, a resistive heating source, a laser and the like. Microwave antenna, optical fibers, resistive heating elements and ultrasound transducers can be substituted for electrodes 18 and 20. When energy source 40 is an RF power supply, 5 to 200 watts, preferably 5 to 100, and still more preferably 5 to 50 watts of electromagnetic energy is delivered from energy source 40 to the electrodes of energy delivery device 16 without impeding out the electrodes.

Electrodes 18 and 20 are electromagnetically coupled to energy source 40. The coupling can be direct from energy source 40 to each electrode 18 and 20 respectively, or indirect by using a collet, sleeve and the like which couples one or more electrodes to energy source 40.

Figure 2A:
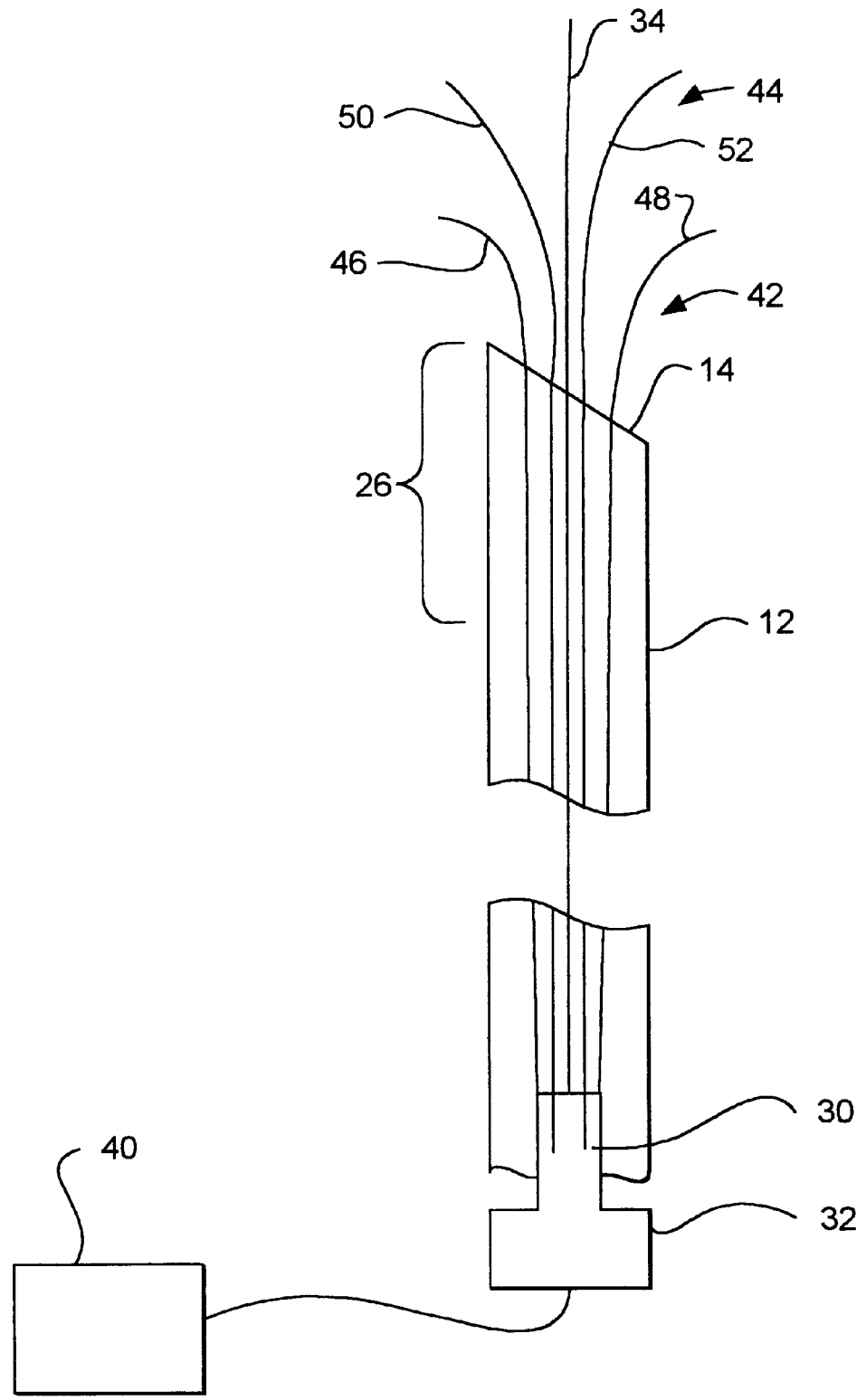
FIG. 2(a) illustrates a cross-sectional view of an embodiment of a cell necrosis apparatus of the present invention with a first and a second set of deployable electrodes.

Referring now to FIG. 2(a), another embodiment of apparatus 10 is shown. Apparatus 10 includes a first set 42 of RF electrodes and a second set 44 of RF electrodes. First and second sets 42 and 44 can include one, two, three, four, five, etc, number of RF electrodes. As illustrated in FIG. 2, first set 42 includes electrodes 46 and 48, and second set 44 includes electrodes 50 and 52. It will be appreciated that first and second sets 42 and 44 can include more or less electrodes than are illustrated in FIG. 2. Electrodes 46, 48, 50 and 52 have tissue piercing distal ends, are positionable in introducer 12 in compacted states, and advanceable to deployed states from distal end 14 with curvature from introducer 12. First set 42 is deployable a greater distance from distal end 14 than second set 44.

First and second sets 42 and 44 are coupled to electrode advancement member 30 and can be simultaneously or individually deployed from distal end 14. Optionally coupled to first set 42, second set 44 and/or electrode advancement member 30 is deployable member 34. Again, deployable member 34 can be coupled to a sensor 36 and all or a portion of deployable member 34 may be an RF electrode.

Figure 2B:
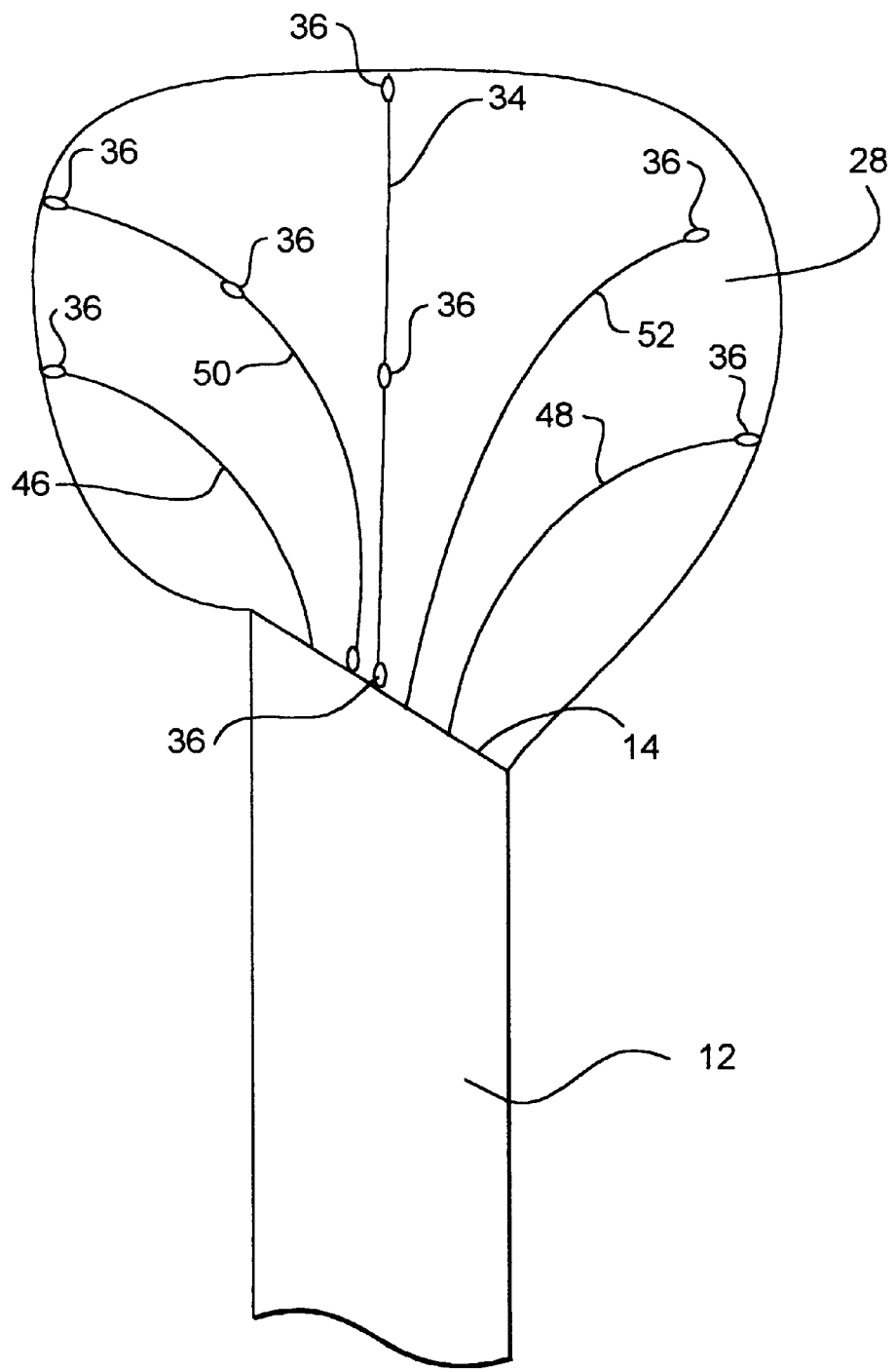
FIG. 2(b) illustrates the cell necrosis apparatus of FIG. 2(a) positioned at a targeted cell necrosis tissue site.

FIG. 2(b) illustrates the use of multiple sensors 36. Sensors 36 can be coupled to all or some of electrodes 46, 48, 50 and/or 52 at different positions of the electrodes. In various embodiments, sensors are positioned at distal ends of electrodes 46 through 52, at positions that are adjacent to distal end 14 of introducer 12, and at sites that are somewhere intermediate between the distal and proximal portions of deployed lengths of the electrodes. Deployable member 34 can include sensors at distal and proximal portions of its deployed length in tissue site 28. The placement of sensors 36 at different locations provides a measurement of temperature and/or impedance, and a determination of the level of cell necrosis, created at tissue site 28.

Figure 3:
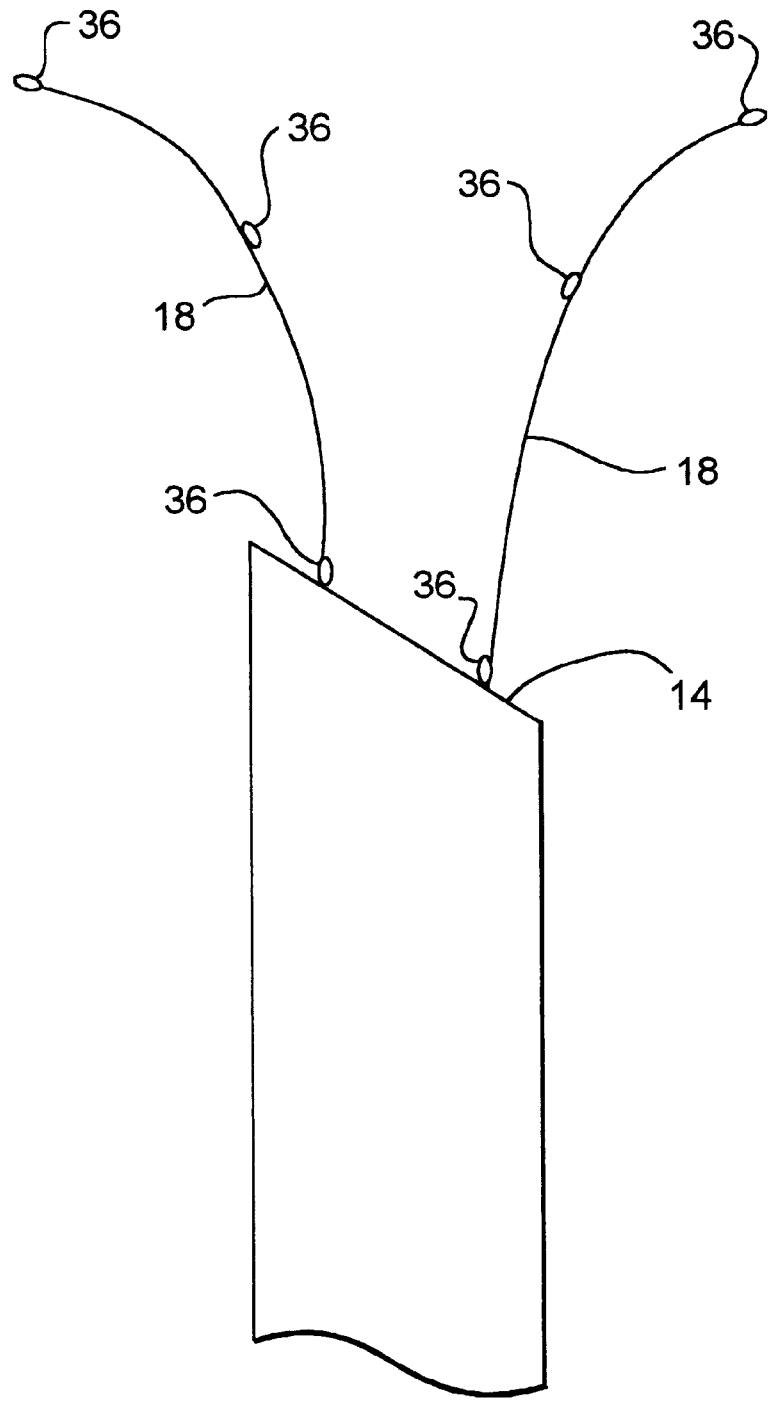
FIG. 3 illustrates an embodiment of a cell necrosis apparatus of the present invention with multiple sensors coupled to electrodes.

As shown in FIG. 3, electrodes 18, 20, 46, 48, 50 and 52, collectively "electrodes 18", can each be coupled to one or more sensors 36. Sensors 36 can be at exterior surfaces of electrodes 18 at their distal ends, intermediate sections as well as adjacent to distal end 14 of introducer 12. Some or all of electrodes 18 and deployable member 34 may have a hollow lumen by which a variety of different fluidic medium can be introduced from proximal to distal ends. Suitable fluidic media include but are not limited to electrolytic solutions, chemotherapeutic agents, drugs, medicaments, gene therapy agents, contrast agents and the like.

Figure 4:
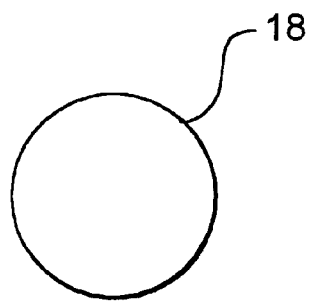
FIG. 4 illustrates a spherical cross-section of an electrode utilized with a cell necrosis apparatus of the present invention.
Figure 5:
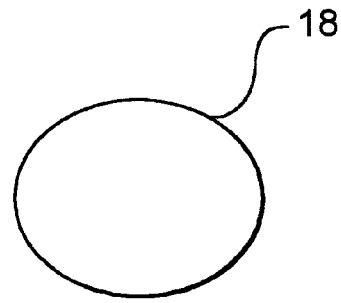
FIG. 5 illustrates an elliptical cross-section of an electrode utilized with a cell necrosis apparatus of the present invention.
Figure 6:
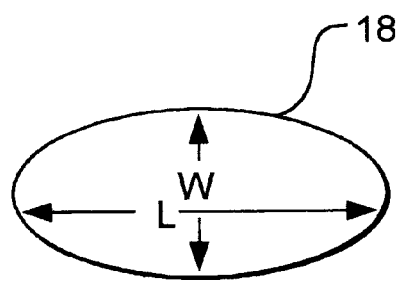
FIG. 6 illustrates a cross-section of an electrode utilized with a cell necrosis apparatus of the present invention with a larger cross-sectional length than its width.
Figure 7:
FIG. 7 illustrates a cross-section of an electrode utilized with a cell necrosis apparatus of the present invention with a flat-like external surface.

Electrode 18, as well as deployable member 34, can have a variety of different geometric cross-sections. Electrodes 18 can be made of conductive solid or hollow straight wires of various shapes such as round, flat, triangular, rectangular, hexagonal, elliptical and the like. FIGS. 4 and 5 illustrate circular and elliptical cross-sections. In FIG. 6, the cross-section has a greater length "L" than a width of "W". If FIG. 7, the cross-sectional is elongated. In various embodiments, the cross-sectional has a greater length than a width in order to enhance ultrasonic viewability.

Figure 8:
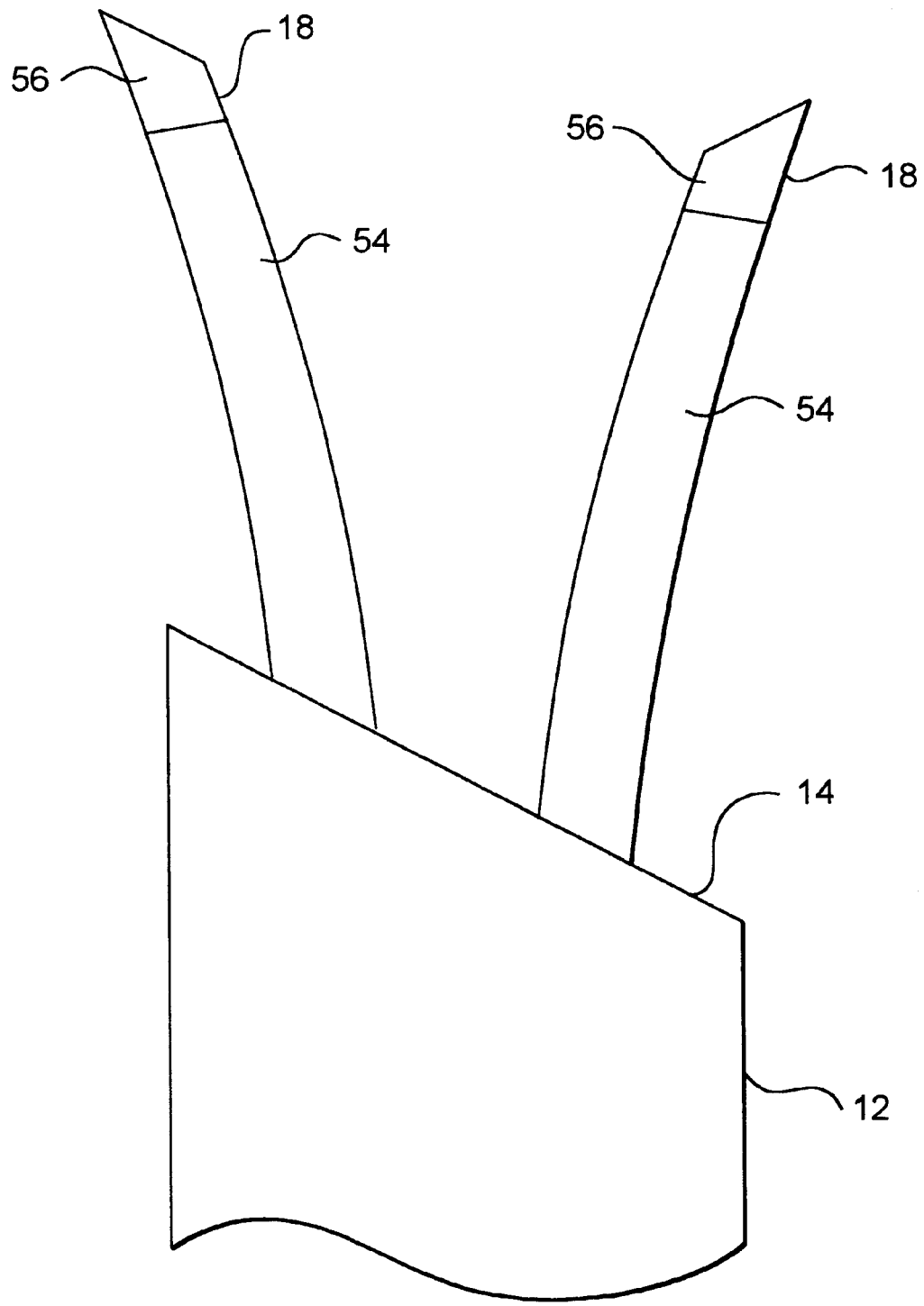
FIG. 8 is a perspective view of a cell necrosis apparatus of the present invention that includes insulation sleeves positioned at exterior surfaces of the electrodes.

Each, a portion of all electrodes 18, as well as deployable member 34, have an exterior surface that is wholly or partially insulated and provide a non-insulated area which is an energy delivery surface. In FIG. 8, two electrodes 18 include insulation 54. In the embodiment of FIG. 8, insulation 54 is a sleeve that can be fixed or adjustable. The active area of electrodes 18 is non-insulated and provides an energy delivery surface 56.

Figure 9:
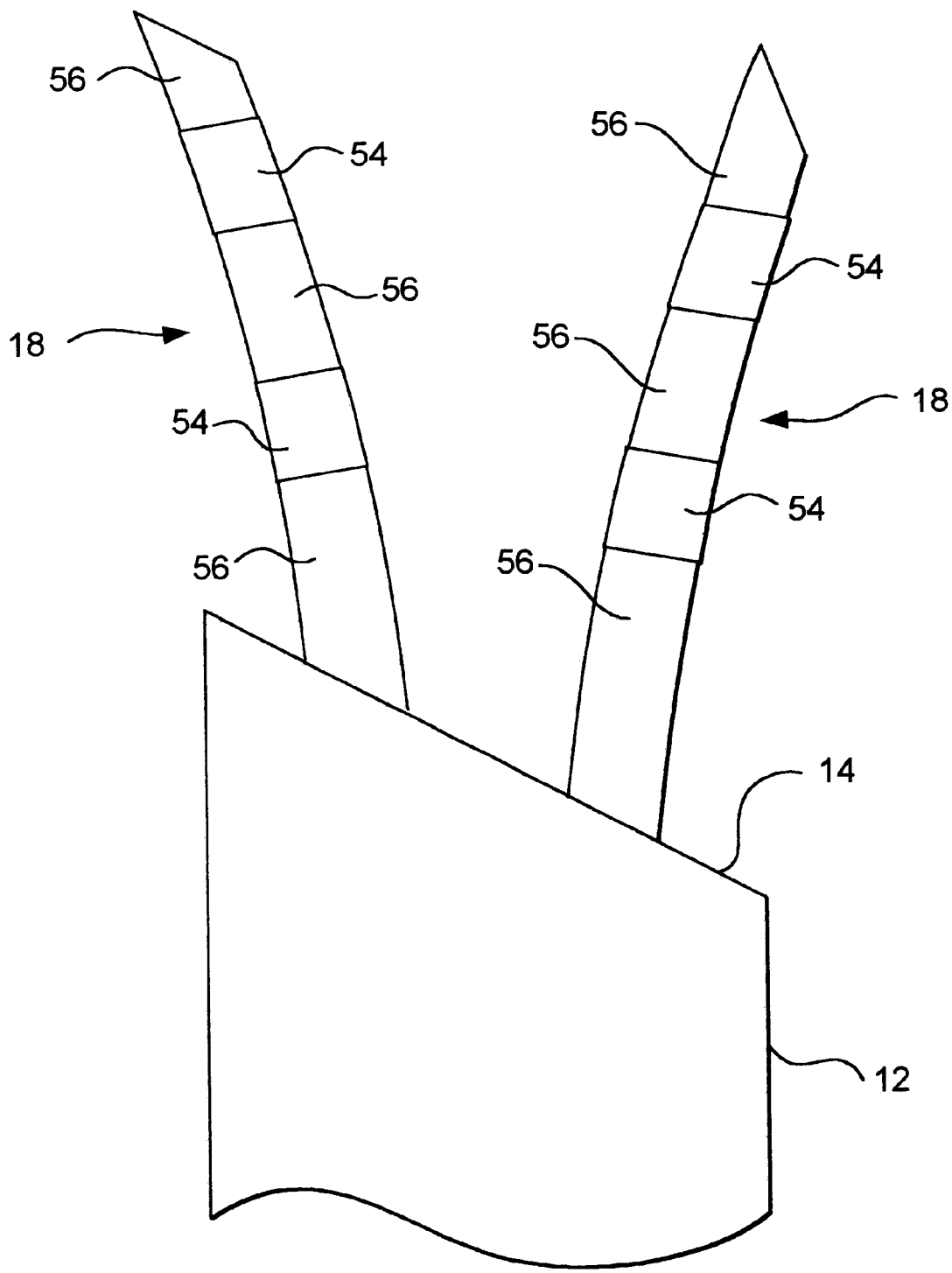
FIG. 9 is a perspective view of a cell necrosis apparatus of the present invention that includes multiple insulation sleeves that circumferentially insulate selected sections of the electrodes.
Figure 10:
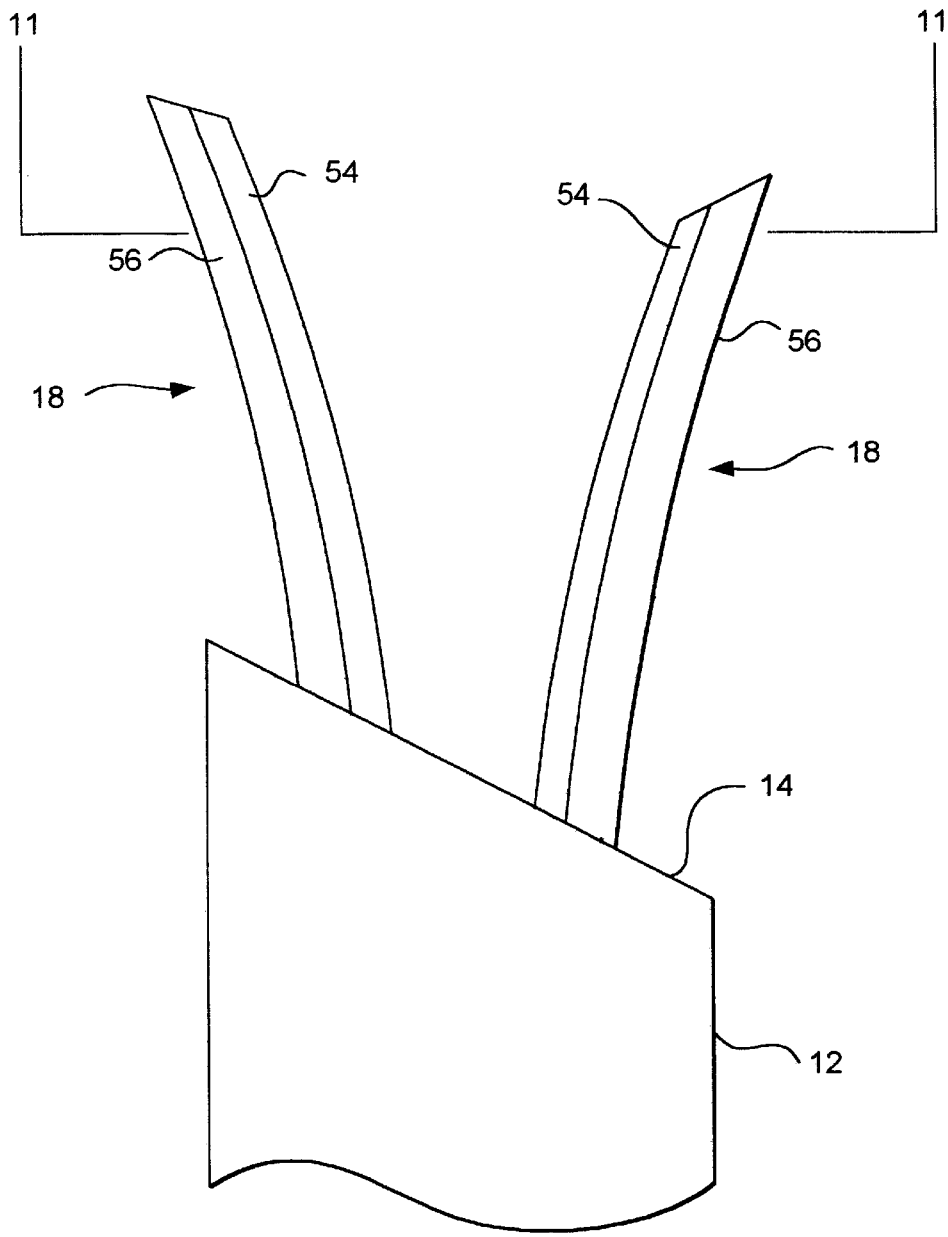
FIG. 10 is a perspective view of a cell necrosis apparatus of the present invention with insulation that extends along longitudinal sections of the electrodes to define adjacent longitudinal energy delivery surfaces.
Figure 11:
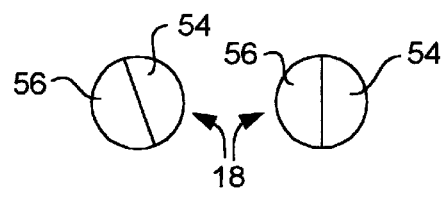
FIG. 11 is a cross-sectional view of the cell necrosis apparatus of FIG. 10 taken along the lines 11—11.

In the embodiment illustrated in FIG. 9, insulation 54 is formed at the exterior of electrodes 18 in circumferential patterns, leaving a plurality of energy delivery surfaces 56. Referring now to the embodiment of FIGS. 10 and 11, insulation 54 extends along a longitudinal exterior surface of electrodes 18. Insulation 54 can extend along a selected distance along a longitudinal length of electrodes 18 and around a selectable portion of a circumference of electrodes 18. In various embodiments, sections of electrodes 18 can have insulation 54 along selected longitudinal lengths of electrodes 18 as well as completely surround one or more circumferential sections of electrodes 18. Insulation 54 positioned at the exterior of electrodes 18 can be varied to define any desired shape, size and geometric energy delivery surface 56.

Figure 12:
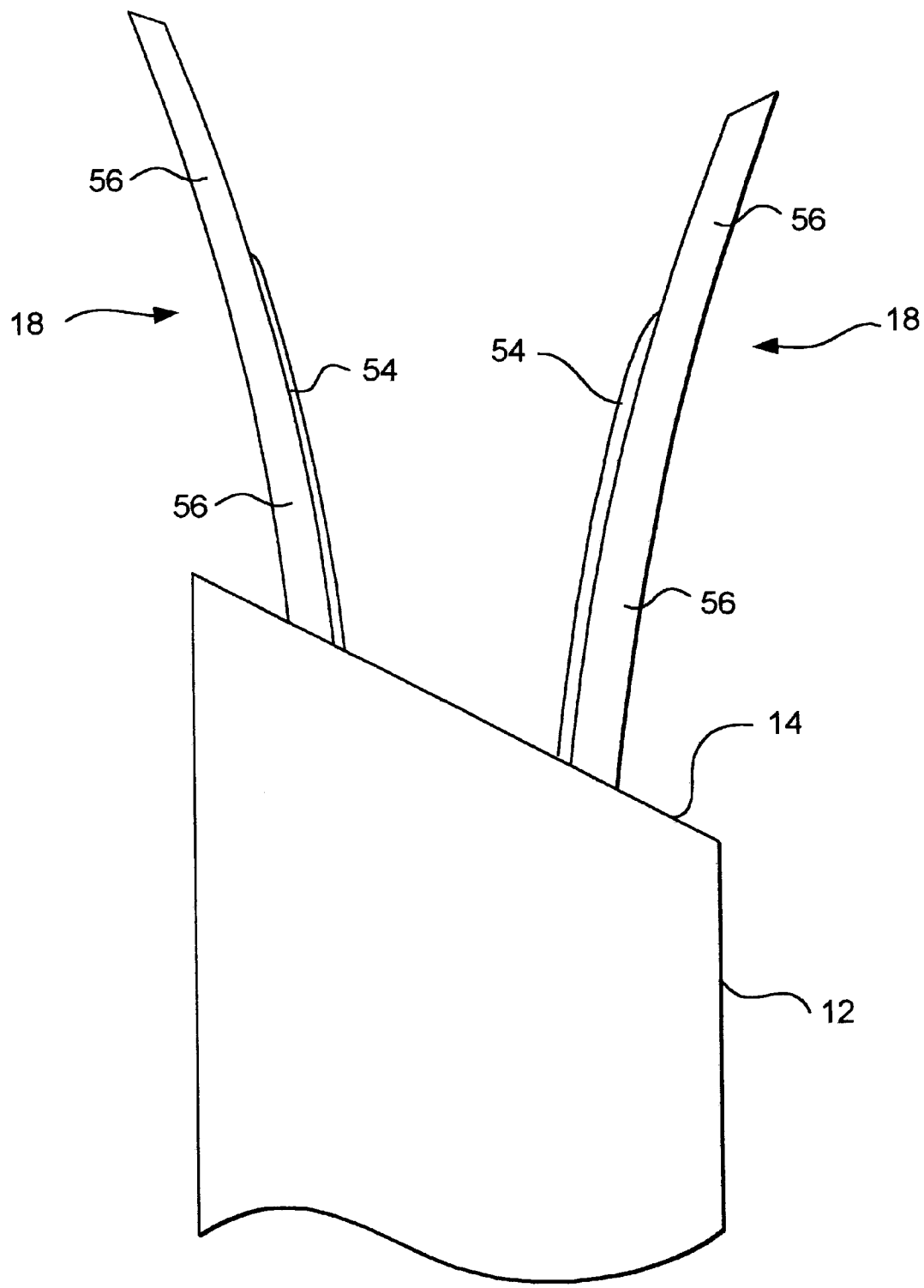
FIG. 12 is a perspective view of a cell necrosis apparatus of the present invention with insulation that extends along longitudinal sections of the electrodes and does not continue to distal ends of the electrodes.
Figure 13:
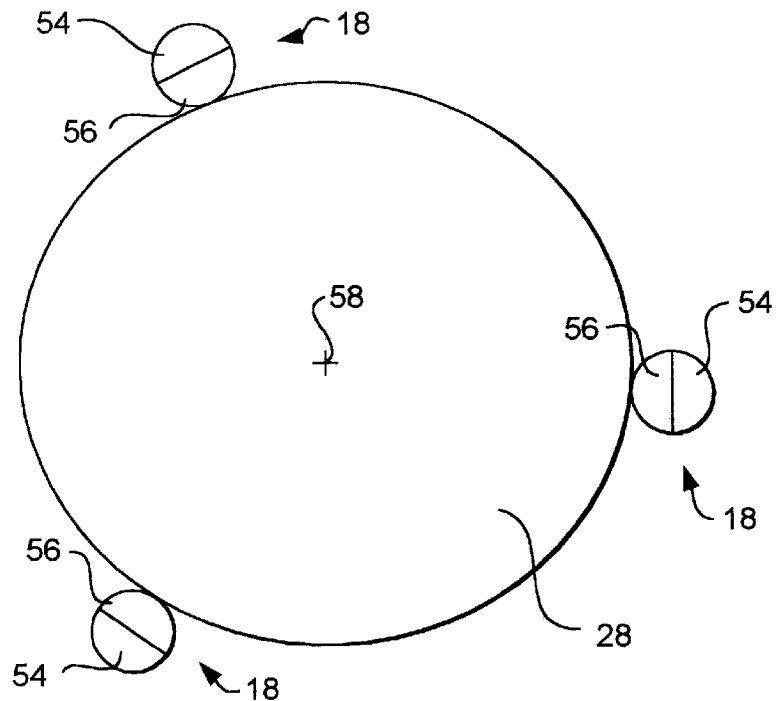
FIG. 13 is a cross-sectional view illustrating the positioning of electrodes adjacent to a selected tissue site with insulation that extends along a longitudinal surface of the electrodes and the insulation faces away from a central axis of the selected tissue site.
Figure 14:
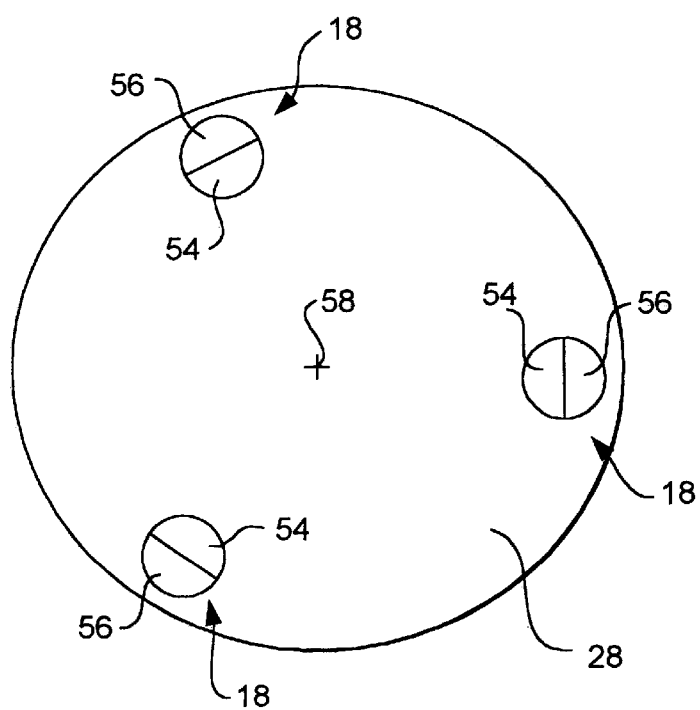
FIG. 14 is a cross-sectional view illustrating the positioning of electrodes at a selected tissue site with insulation that extends along a longitudinal surface of the electrodes and the insulation faces toward a central axis of the selected tissue site.

In FIG. 12, insulation 54 is disposed on only one section of a deployed length of electrodes 18. Energy delivery surfaces 56 are at distal portions of electrodes 18 as well as on longitudinal surfaces adjacent to insulation 54. In FIG. 13, insulation 54 extends along a longitudinal length of electrodes 18 can face toward a central axis 58 of tissue site 28 and energy delivery surface 56 faces towards in a direction toward the central axis 58. In FIG. 14, insulation 54 extends along a longitudinal length of electrodes 18 and faces away from central axis 58 with energy delivery surface 56 facing away from central axis 58. In the embodiments illustrated in FIGS. 12 and 13, three electrodes 18 are positioned inside or outside of a periphery of tissue site 28. It will be appreciated that any number of electrodes 18 can be deployed with and without insulation to created a selectable cell necrosis pattern.

Electrodes 18 are selectably deployable from introducer 12 with curvature to create any desired geometric area of cell necrosis. The selectable deployment is achieved by having electrodes 18 with, (i) different advancement lengths from introducer 12, (ii) different deployed geometric configurations, (iii) variations in cross-sectional geometries, (iv) selectable insulation provided at each and/or all of the deployed electrodes 18, or (v) the use of adjustable insulation.

Deployed electrodes 18 can create a variety of different geometric cell necrosis zones including but not limited to spherical, semi-spherical, spheroid, triangular, semi-triangular, square, semi-square, rectangular, semi-rectangular, conical, semi-conical, quadrilateral, semi-quadrilateral, semi-quadrilateral, rhomboidal, semi-rhomboidal, trapezoidal, semi-trapezoidal, combinations of the preceding, geometries with non-planar sections or sides, free-form and the like.

Figure 15:
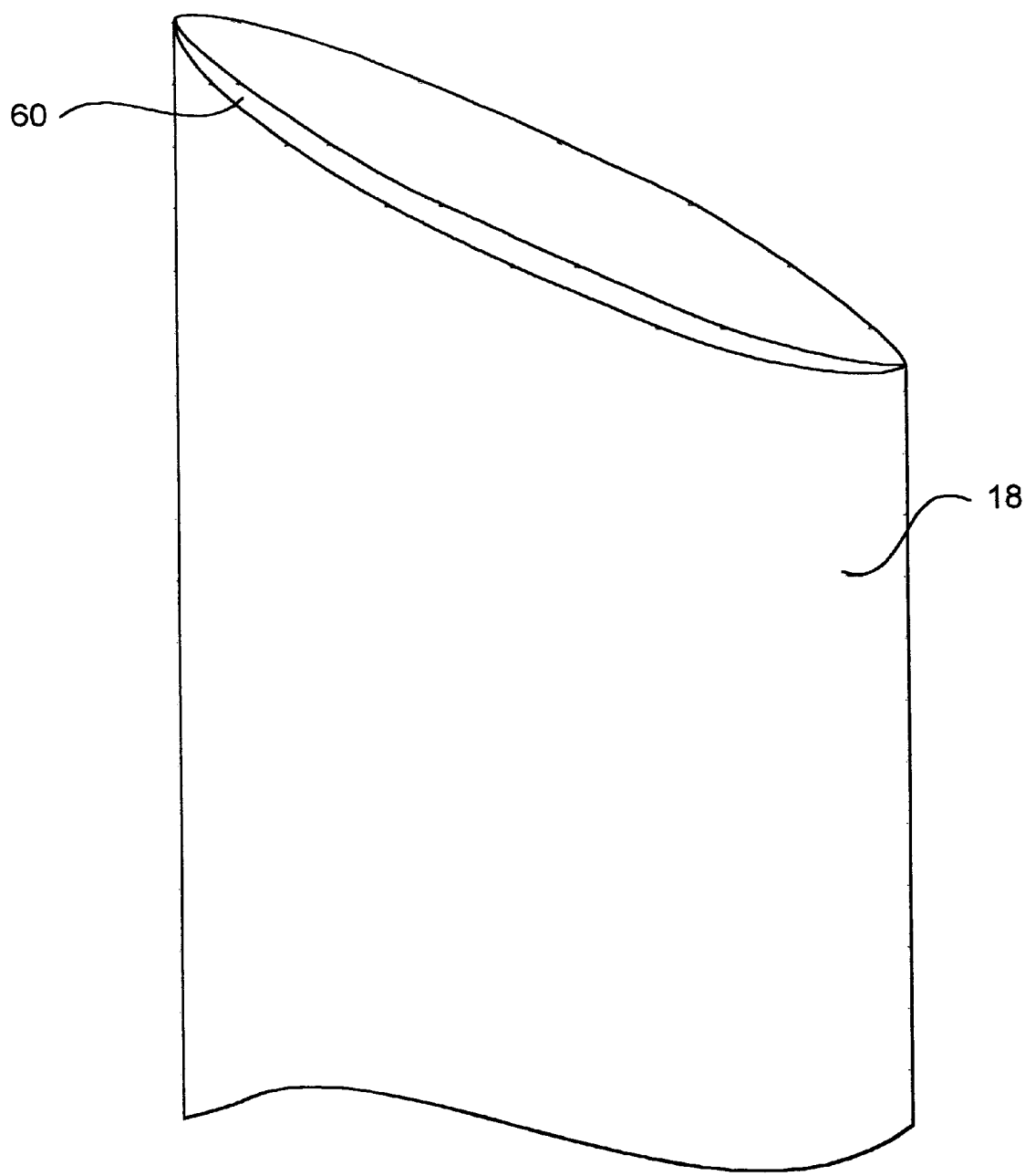
FIG. 15 is a close-up perspective view of a surface area of an electrode body at a distal end of an electrode of a cell necrosis apparatus of the present invention.

In one embodiment, the ultrasonic visibility of electrodes 18 through is enhanced by creating a larger electrode distal end surface area 60. Surface area 60 is the amount of the electrode body that is at the distal end of electrodes 18. Referring now to FIG. 15 the distal end of electrode 18 has at cut angle of at least 25°, and in another embodiment the cut angle is at least 30°. This creates a larger surface area 60. The distal end of deployable member 34 can also have these cut angles.

Figure 16:
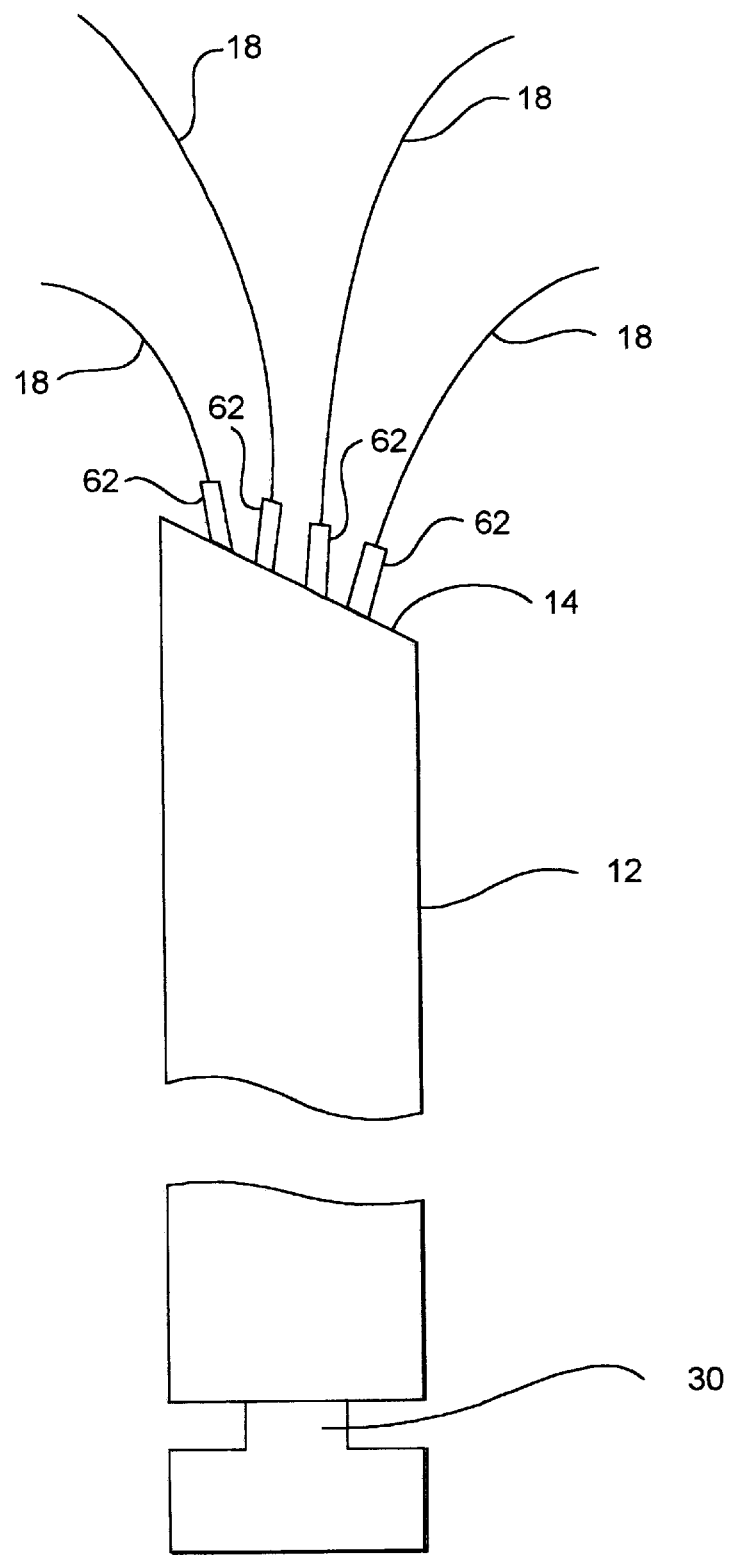
FIG. 16 is a perspective view of a cell necrosis apparatus of the present invention with spacers associated with each deployed electrode.
Figure 17:
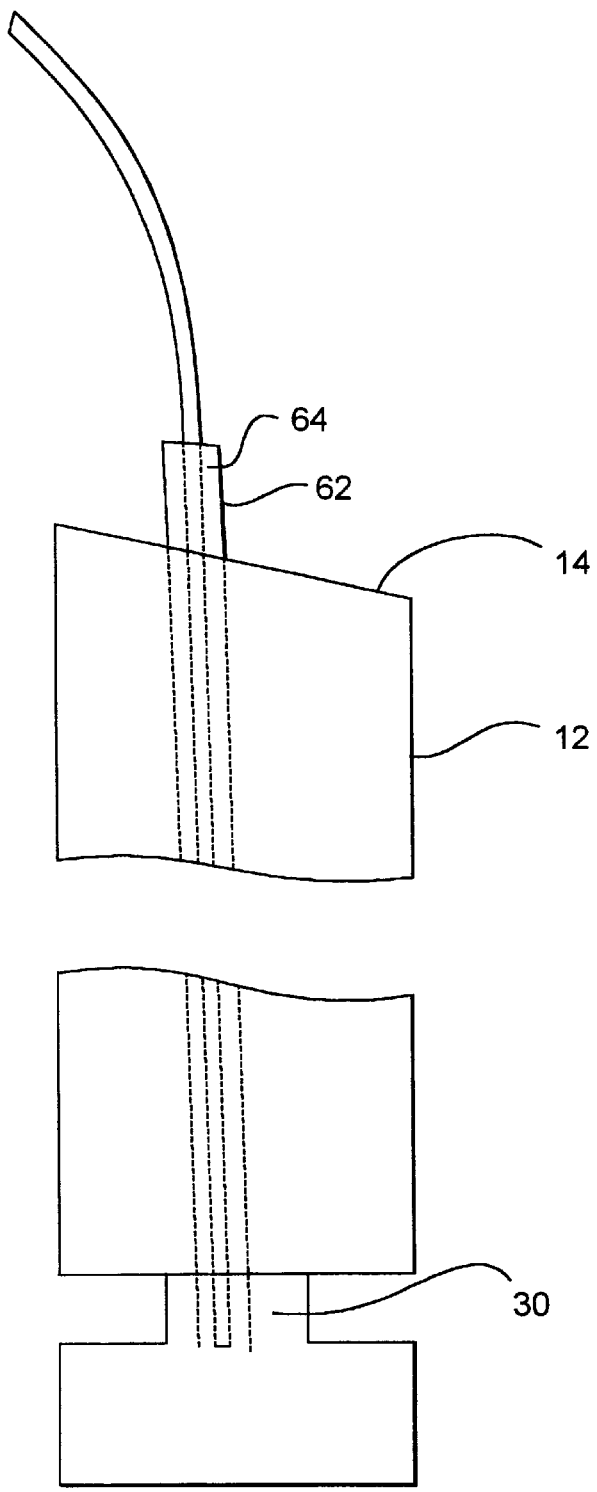
FIG. 17 is a cross-sectional view of a cell necrosis apparatus of the present invention illustrating a spacer, an associated electrode and insulation inside the spacer.

Referring to FIGS. 16 and 17, each or selected electrodes 18 and deployable member 34 can have an associated spacer 62. Spacers 62 are advanceable from distal end 14 of introducer 12 and can be coupled to advancement member 30. Spacers 62 create a physical spacing that separates the deployed electrodes 18 from each other. The spacing created by spacers 62 also forms an area in tissue site 28 where there is reduced or very little cell necrosis. Positioned within spacers 62 is an insulation 64 that electrically and electromagnetically isolates electrodes 18 from spacers 62.

Figure 18:
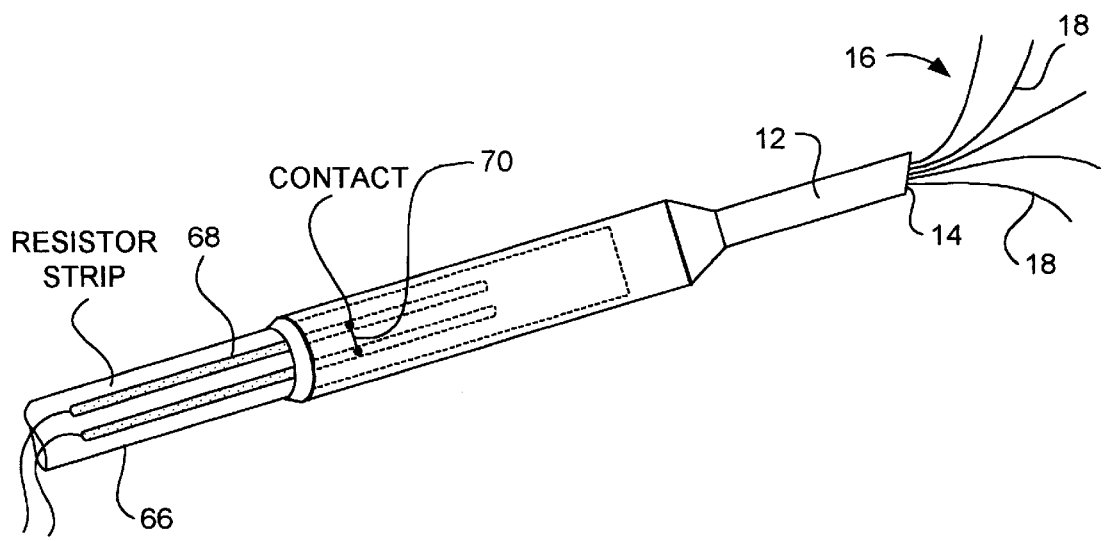
FIG. 18 is a cross-sectional view of an embodiment of a cell necrosis apparatus of the present invention that includes a slidable member that engages a power source to a contact coupled to the electrodes.
Figure 19:
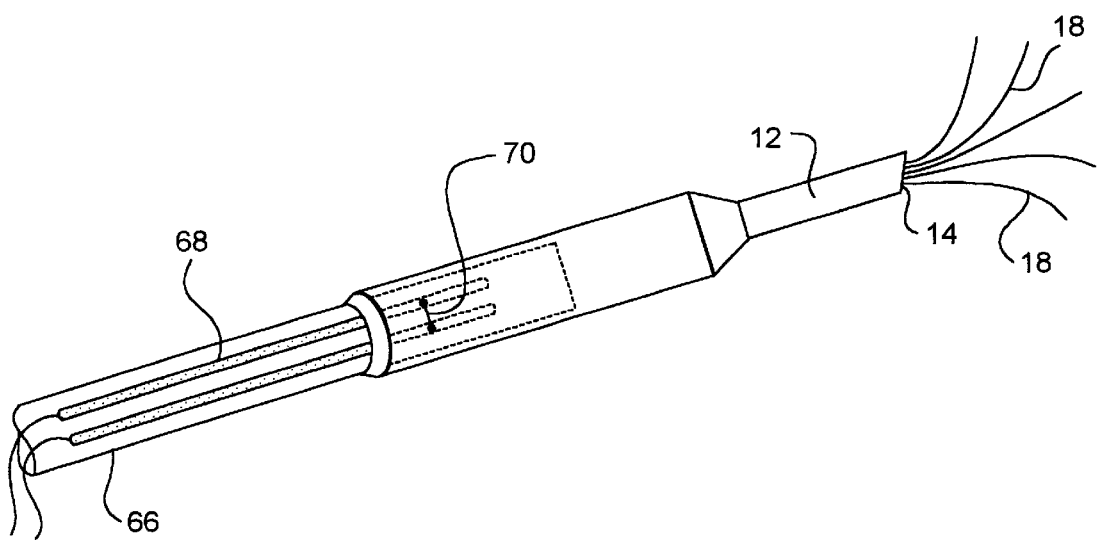
FIG. 19 is a cross-sectional view of the apparatus of FIG. 18 with the slidable member pulled back and disengaging the power source from the electrodes.

As illustrates in FIGS. 18 and 19, apparatus 10 can include a slidable member 66 that provides an electrical connection between energy delivery 16 and energy source 40. Slidable member 66 can be advancement member 30 or a handpiece. In one embodiment, slidable member 66 has one or two electrical contact pads 68 which can be resistor strips. When slidable member is moved in a distal direction relative to distal end 14 of introducer 12 resistor strips 68 becomes engaged with a contact 70 (FIG. 18). Contact 70 is coupled to energy delivery device 16. When resistor strips 68 are engaged with contact 70, power and energy is delivered from energy source to electrodes 18. Slidable member 66 is then moved in a distal direction and resistor strips become un-engaged with contact 70 and the delivery of power from energy source 40 is disrupted (FIG. 19). The employment of slidable member 66 provides a convenient energy delivery device 16 on and off mechanism at the hand of the physician.

Resistor strips 68 can be used as sensors to recognize a variable setting of one or all of electrodes 18 of energy delivery device 16. Resistor strips 68 can be used to measure resistance at a setting so that a change in the resistance value can be measured as slidable member 66 is moved and a corresponding change in the energy delivery surface corresponding to the electrodes 18. The resistance value can be correlated to determine an optimal power in delivering energy from energy source 40. Gap sensors, including but not limited to lasers and ultrasound, can be used to determine the variable setting.

Figure 20:
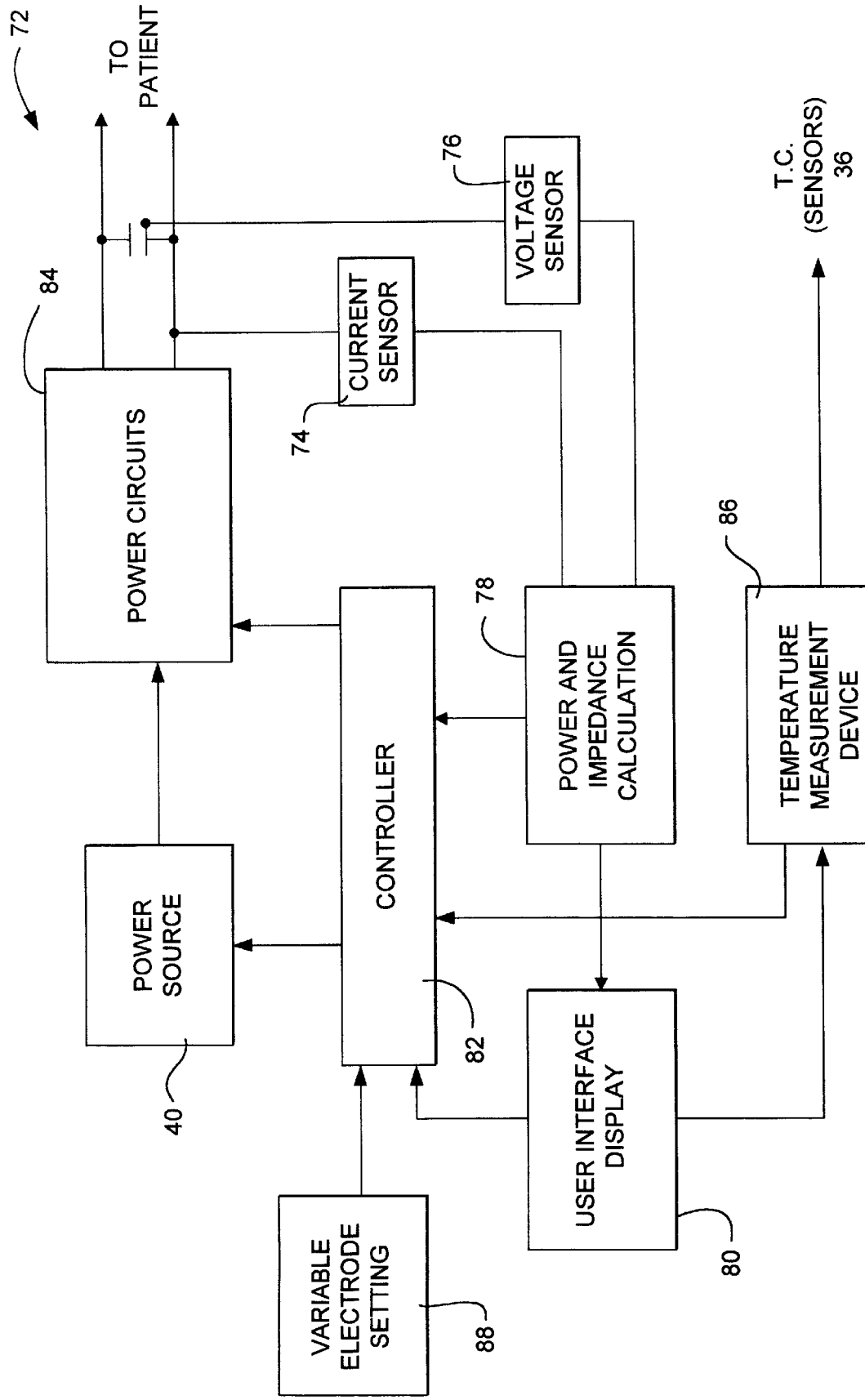
FIG. 20 is a block diagram illustrating the inclusion of a controller, electromagnetic energy source and other electronic components of the present invention.

Referring now to FIG. 20, a feedback control system 72 is connected to energy source 40, sensors 36 and energy delivery device 16. Feedback control system 72 receives temperature or impedance data from sensors 36 and the amount of electromagnetic energy received by energy delivery device 16 is modified from an initial setting of cell necrosis energy output, cell necrosis time, temperature, and current density (the "Four Parameters"). Feedback control system 72 can automatically change any of the Four Parameters. Feedback control system 72 can detect impedance or temperature and change any of the Four Parameters. Feedback control system 72 can include a multiplexer to multiplex different electrodes 18 and a temperature detection circuit that provides a control signal representative of temperature or impedance detected at one or more sensors 36. A microprocessor can be connected to the temperature control circuit.

The user of apparatus 10 can input an impedance value which corresponds to a setting position located at apparatus 10. Based on this value, along with measured impedance values, feedback control system 72 determines an optimal power and time need in the delivery of RF energy. Temperature is also sensed for monitoring and feedback purposes. Temperature can be maintained to a certain level by having feedback control system 72 adjust the power output automatically to maintain that level.

In another embodiment, feedback control system 72 determines an optimal power and time for a baseline setting. Ablation volumes or lesions are formed at the baseline first.

Larger lesions can be obtained by extending the time of ablation after a center core is formed at the baseline. A completion of lesion creation can be checked by advancing energy delivery device 16 from distal end 14 of introducer 12 to a desired lesion size and by monitoring the temperature at the periphery of the lesion.

In another embodiment, feedback control system 72 is programmed so the delivery of energy to energy delivery device 16 is paused at certain intervals at which time temperature is measured. By comparing measured temperatures to desired temperatures feedback control system 72 can terminate or continue the delivery of power to electrodes 18 for an appropriate length of time.

The following discussion pertains particularly to the use of an RF energy source and RF electrodes but applies to other energy delivery devices and energy sources including but not limited to microwave, ultrasound, resistive heating, coherent and incoherent light, and the like.

Current delivered to electrodes 18 is measured by a current sensor 74. Voltage is measured by voltage sensor 76. Impedance and power are then calculated at power and impedance calculation device 78. These values can then be displayed at user interface and display 80. Signals representative of power and impedance values are received by controller 82.

A control signal is generated by controller 82 that is proportional to the difference between an actual measured value, and a desired value. The control signal is used by power circuits 84 to adjust the power output in an appropriate amount in order to maintain the desired power delivered at energy delivery device 16.

In a similar manner, temperatures detected at sensors 36 provide feedback for determining the extent of cell necrosis, and when a completed cell necrosis has reached the physical location of sensors 36. The actual temperatures are measured at temperature measurement device 86 and the temperatures are displayed at user interface and display 80. A control signal is generated by controller 82 that is proportional to the difference between an actual measured temperature, and a desired temperature. The control signal is used by power circuits 84 to adjust the power output in an appropriate amount in order to maintain the desired temperature delivered at the respective sensor 36. A multiplexer can be included to measure current, voltage and temperature, at the numerous sensors 36, and energy is delivered to energy delivery device 16. A variable electrode setting 88 is coupled to controller 82.

Controller 82 can be a digital or analog controller, or a computer with software. When controller 82 is a computer it can include a CPU coupled through a system bus. On this system can be a keyboard, a disk drive, or other non-volatile memory systems, a display, and other peripherals, as are known in the art. Also coupled to the bus are a program memory and a data memory.

User interface and display 80 includes operator controls and a display. Controller 82 can be coupled to imaging systems, including but not limited to ultrasound, CT scanners, X-ray, MRI, mammographic X-ray and the like. Further, direct visualization and tactile imaging can be utilized.

The output of current sensor 74 and voltage sensor 76 is used by controller 82 to maintain a selected power level at energy delivery device 16. The amount of RF energy delivered controls the amount of power. A profile of power delivered can be incorporated in controller 82, and a preset amount of energy to be delivered can also be profiled.

Circuitry, software and feedback to controller 82 result in process control, and the maintenance of the selected power, and are used to change, (i) the selected power, including RF, microwave, laser and the like, (ii) the duty cycle (on-off and wattage), (iii) bi-polar or mono-polar energy delivery and (iv) infusion medium delivery, including flow rate and pressure. These process variables are controlled and varied, while maintaining the desired delivery of power independent of changes in voltage or current, based on temperatures monitored at sensors 36.

Figure 21:
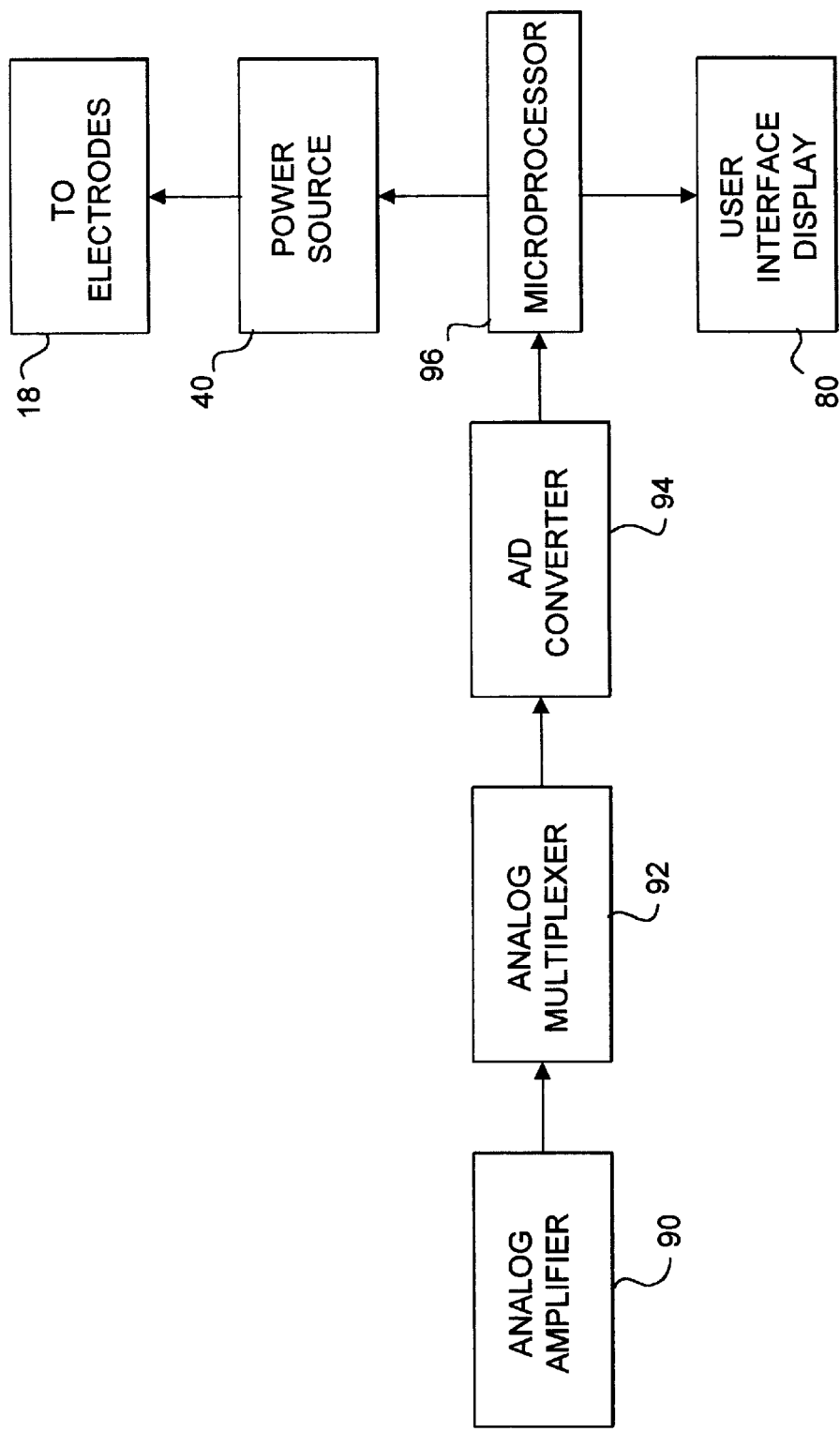
FIG. 21 is a block diagram illustrating an analog amplifier, analog multiplexer and microprocessor used with the present invention.

Referring now to FIG. 21, current sensor 74 and voltage sensor 76 are connected to the input of an analog amplifier 90. Analog amplifier 90 can be a conventional differential amplifier circuit for use with sensors 36. The output of analog amplifier 90 is sequentially connected by an analog multiplexer 46 to the input of A/D converter 92. The output of analog amplifier 90 is a voltage which represents the respective sensed temperatures. Digitized amplifier output voltages are supplied by A/D converter 92 to a microprocessor 96. Microprocessor 96 may be Model No. 68HCII available from Motorola. However, it will be appreciated that any suitable microprocessor or general purpose digital or analog computer can be used to calculate impedance or temperature.

Microprocessor 96 sequentially receives and stores digital representations of impedance and temperature. Each digital value received by microprocessor 96 corresponds to different temperatures and impedances.

Calculated power and impedance values can be indicated on user interface and display 80. Alternatively, or in addition to the numerical indication of power or impedance, calculated impedance and power values can be compared by microprocessor 96 with power and impedance limits. When the values exceed predetermined power or impedance values, a warning can be given on user interface and display 80, and additionally, the delivery of RF energy can be reduced, modified or interrupted. A control signal from microprocessor 96 can modify the power level supplied by energy source 40.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. A cell necrosis apparatus, comprising:
   an introducer with a distal end sufficiently sharp to penetrate tissue; and
   an energy delivery device including a first set of RP electrodes and a second set of RF electrodes both having a tissue piercing distal end and positionable in the introducer as the introducer is advanced through tissue, the first and second sets of RF electrodes being deployable with curvature from the introducer, deployed portions of the electrodes of the first and second sets of electrodes being configured to create substantially the same geometric ablation shape at a first deployed position and a second deployed position.

2. The apparatus of claim 1, wherein at least one electrode of the first or second sets of electrode has a substantially oval cross section or a substantially elliptical cross section.

3. The apparatus of claim 1, further comprising: a sensor coupled to at least one of the energy delivery device, the first set of electrode or the second set of electrode.

4. The apparatus of claim 3, wherein the sensor is configured to detect a characteristic of a tissue site.

5. The apparatus of claim 3, wherein the sensor is one of an impedance sensor, a thermal sensor, a thermocouple, an optical sensor or an optical fiber.

6. A cell necrosis apparatus, comprising,
an introducer with a distal end sufficiently sharp to penetrate tissue; and
an energy delivery device including a first set of RF electrodes, a second set of RF electrodes and a third RF electrode all having a tissue piercing distal end and positionable in the introducer as the introducer is advanced through tissue, the first and second sets of RF electrodes being deployable with curvature from the introducer, the third RF electrode being deployable from the introducer with less curvature than the first and second sets of RF electrodes, each of a deployed portion of the electrodes of the first and second sets of electrodes and the third electrode being configured to increase in length as the first and second sets of electrodes and third of electrode are distally advanced from the introducer such that the first and second sets of electrodes and third electrode create substantially the same geometric ablation shape independent of distance deployed from the distal end of the introducer.

7. The apparatus of claim 6, wherein the third electrode is deployable from the introducer substantially without curvature.

8. The apparatus of claim 6, further comprising:
an RF electrode advancement member coupled to the first set of RF electrodes, the second set of RF electrodes and the third RF electrode.

9. The apparatus of claim 6, wherein the introducer is configured to receive a fluidic medium.

10. The apparatus of claim 6, further comprising:
an insulator positioned in a surrounding relation to at least a portion of the introducer.

11. The apparatus of claim 6, further comprising:
an insulator positioned in a surrounding relation to at least a portion of the first and second sets of RF electrodes.

12. The apparatus of claim 6, further comprising:
a sensor coupled to one of an electrode of the first set of RF electrodes.

13. The apparatus of claim 6, further comprising:
a sensor coupled to one of an electrode of the second set of RF electrodes.

14. The apparatus of claim 6, further comprising:
a sensor coupled to the third RF electrode.

15. The apparatus of claim 6, further comprising:
a sensor coupled to the introducer.

16. The apparatus of claim 6, further comprising:
a sensor coupled to the energy delivery device.

17. The apparatus of claim 6, wherein at least a portion of at least one electrode of at least the first or the second set of RF electrodes is formed of a shaped memory alloy.

18. The apparatus of claim 16, further comprising:
a feedback control coupled to the sensor and the energy delivery device.

19. The apparatus of claim 6, further comprising:
an impedance measurement apparatus coupled to at least one electrode of the first set of RP electrodes, the second set of RF electrodes, or the third RF electrode.

20. The apparatus of claim 19, wherein the impedance measurement apparatus comprises:
a sensor positioned on at least one electrode of the first set of RF electrodes, the second set of RF electrodes, or the third RF electrode, the sensor detecting a characteristic of a tissue site using a measurement of a voltage and/or current;
a controller coupled to the sensor to output a control signal;
a processor coupled to the controller; and
a power source coupled to the controller to deliver RF energy to a tissue site, an amount of RF energy provided by the power source to the tissue site being affected by the control signal from the controller.

21. The apparatus of claim 6, wherein the introducer is a flexible introducer.

22. The apparatus of claim 6, wherein at least a portion of the introducer is an energy delivery device.

23. The apparatus of claim 6, wherein a distal portion of the introducer is an RF electrode.

24. The apparatus of claim 6, wherein at least one of the electrodes of the first or second sets of electrode or the third electrode has a substantially oval cross section or a substantially elliptical cross section.

25. A cell necrosis apparatus, comprising:
an introducer including a lumen and a distal end sufficiently sharp to penetrate tissue;
an energy delivery device including a first RF electrode with a tissue piercing distal portion and a second RF electrode with a tissue piercing distal portion, the first and second RF electrodes being positionable in the introducer as the introducer is advanced through tissue and deployable with curvature from the introducer at a selected tissue site, each of a deployed portion of the first and second electrodes electrode being configured to increase in length as the first and second set electrodes are distally advanced from the introducer such that the first and second electrodes create substantially the same geometric ablation shape independent of distance deployed from the distal end of the introducer;
a deployable member coupled to the first and second RF electrodes; and
a first sensor coupled to the deployable member to advance through tissue with the deployable member towards the selected tissue site.

26. The apparatus of claim 25, wherein the first sensor is a thermal sensor.

27. The apparatus of claim 25, further comprising:
a cooling medium employed with at least one of the deployable member, the first RF electrode or the second RF electrode.

28. The apparatus of claim 25, further comprising:
an RF electrode advancement member coupled to the first and second RF electrodes and configured to advance the first and second RF electrodes through tissue.

29. The apparatus of claim 25, wherein the introducer is configured to receive a fluidic medium.

30. The apparatus of claim 25, wherein the first RF electrode includes a hollow lumen configured to receive a fluidic medium.

31. The apparatus of claim 25, further comprising:
an insulator positioned in a surrounding relation to at least a portion of the introducer.

32. The apparatus of claim 25, further comprising:
an insulator positioned in a surrounding relation to at least a portion of the first RF electrode.

33. The apparatus of claim 25, further comprising:
an insulator positioned in a surrounding relation to at least a portion of the second RF electrode and an insulator positioned in a surrounding relation to at least a portion of the first and second RF electrodes.

34. The apparatus of claim 25, further comprising: an obturator coupled to the deployable member.

35. The apparatus of claim 34, wherein the obturator has a tissue piercing distal end.

36. The apparatus of claim 34, wherein the obturator is positionable in the elongated member.

37. The apparatus of claim 25, further comprising:
a second sensor coupled to the first RF electrode.

38. The apparatus of claim 25, wherein the second sensor is a thermal sensor.

39. The apparatus of claim 25, further comprising:
a third sensor coupled to the introducer.

40. The apparatus of claim 25, wherein the first RF electrode is formed of a shaped memory alloy.

41. The apparatus of claim 25, wherein the first RF electrode is formed of stainless steel.

42. The apparatus of claim 25, wherein the first and second RF electrodes are deployable to surround the selected tissue site.

43. The apparatus of claim 42, wherein the first and second RF electrodes are deployable to surround a tumor.

44. The apparatus of claim 43, wherein the introducer is introduced through the selected tissue site and the first and second RF electrodes are deployable to surround the selected tissue site.

45. The apparatus of claim 35, further comprising:
a feedback control coupled to the first sensor and the first RF electrode.

46. The apparatus of claim 25, further comprising: an impedance measurement apparatus coupled to at least one of the first electrode or the second electrode.

47. The apparatus of claim 46, wherein the impedance measurement apparatus comprises:
a sensor positioned on at least one of the first electrode or the second electrode, the sensor detecting a characteristic of a tissue site using a measurement of a voltage and/or current;
a controller coupled to the sensor to output a control signal;
a processor coupled to the controller; and
a power source coupled to the controller to deliver RF energy to the selected tissue site, an amount of RF energy provided by the power source to the tissue site being affected by the control signal from the controller.

48. The apparatus of claim 25, wherein the introducer is a flexible introducer.

49. The apparatus of claim 25, wherein at least a portion of the introducer is an energy delivery device.

50. The apparatus of claim 25, wherein a distal portion of the introducer is an RF electrode.

51. The apparatus of claim 25, further comprising a groundpad electrode coupled to the first and second electrodes.

52. The apparatus of claim 25, wherein the deployable member is a return electrode.

53. A cell necrosis apparatus, comprising:
an introducer with a distal end sufficiently sharp to penetrate tissue; and an energy delivery device including a first set of RF electrodes and a second set of RF electrodes both having a tissue piercing distal end and positionable in the introducer as the introducer is advanced through tissue, the first and second sets of RF electrodes being deployable with curvature from the introducer, each of a deployed portion of the electrodes of the first and second sets of electrodes being configured to create substantially the same geometric ablation shape independent of distance deployed from the introducer.

54. A cell necrosis apparatus, comprising:
an introducer with a distal end sufficiently sharp to penetrate tissue; and
an energy delivery device including a first set and a second set of optical fibers both positionable in the introducer as the introducer is advanced through tissue, the first and second sets of optical fibers being deployable with curvature from the introducer, each of a deployed portion of the first and second sets of optical fibers being configured to create substantially the same geometric ablation shape independent of distance deployed from the introducer.

55. The apparatus of claim 54 farther comprising:
a laser coupled to the optical fiber.

56. A cell necrosis apparatus, comprising:
an introducer means with a distal end sufficiently sharp to penetrate tissue; and
an energy delivery device means including a first set of electrode means and a second set of electrode means both having a tissue piercing distal end and positionable in the introducer means as the introducer means is advanced through tissue, the first and second set of electrodes means being deployable with curvature from the introducer means, each of a deployed portion of the electrodes of the first and second set of electrode means being configured to create substantially the same geometric ablation shape independent of distance deployed from the distal end of the introducer means.

* * * * *

UNITED STATES PATENT AND TRADEMARK OFFICE
CERTIFICATE OF CORRECTION

| | | |
|---|---|---|
| PATENT NO. | : 6,235,023 B1 | Page 1 of 1 |
| APPLICATION NO. | : 09/148571 | |
| DATED | : May 22, 2001 | |
| INVENTOR(S) | : Kee S. Lee, Daniel Balbierz and Edward J. Gough | |

It is certified that error appears in the above-identified patent and that said Letters Patent is hereby corrected as shown below:

On the Title Page Item (75) Inventors: please add

Edward J. Gough, Menlo Park, CA (US)

Signed and Sealed this

Second Day of January, 2007

JON W. DUDAS
*Director of the United States Patent and Trademark Office*